United States Patent [19]
Fujii et al.

[11] Patent Number: 5,885,816
[45] Date of Patent: Mar. 23, 1999

[54] CATALYTIC ANTIBODIES ENANTIOSELECTIVELY HYDROLYSING AMINO ACID ESTER DERIVATIVES

[75] Inventors: Ikuo Fujii; Fujie Tanaka, both of Suita; Keiko Kinoshita, Minoo, all of Japan

[73] Assignee: Protein Engineering Research Institute, Osaka, Japan

[21] Appl. No.: 737,129

[22] PCT Filed: Mar. 17, 1995

[86] PCT No.: PCT/JP95/00462

§ 371 Date: Nov. 15, 1996

§ 102(e) Date: Nov. 15, 1996

[87] PCT Pub. No.: WO96/29426

PCT Pub. Date: Sep. 26, 1996

[51] Int. Cl.[6] .............................. C12N 9/00; C12N 5/12; C12S 13/00
[52] U.S. Cl. ................. 435/188.5; 435/280; 435/346
[58] Field of Search ................. 435/188.5, 280, 435/346

[56] References Cited

U.S. PATENT DOCUMENTS 5,190,865  3/1993  Schultz ........................ 435/108
5,250,426  10/1993  Lerner et al. ................. 435/146

OTHER PUBLICATIONS

Tanaka, F., et al. (1996) J. Amer. Chem Soc. 118, 2332–2339.
Pollack, S. J., et al., (1989) J. Am. Chem. Soc. 111, 5961–5962.
Guo, J., et. al. (1994) J. Am. Chem. Soc. 116, 6062–6069.

*Primary Examiner*—Charles L. Patterson, Jr.
*Attorney, Agent, or Firm*—Wenderoth, Lind & Ponack, L.L.P.

[57] ABSTRACT

A process for conducting optical resolution of a racemic mixture of an amino acid derivatives and a process for preparing an optically active amino acid using a catalytic antibody enantioselectively hydrolyzing an amino acid ester derivative are provided. The catalytic antibody and hybridoma producing said antibody are also provided. The hybridomas in the present invention are typically produced by stimulation with an antigen comprising as a hapten a compound of the formula:

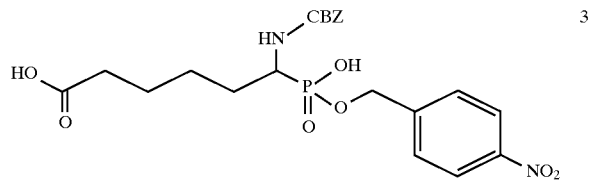

wherein CBZ is N-benzyloxycarbonyl.

30 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 636 bases
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CTCGAGTCTG  GGACTGAACT  GGCAAAACCT  GGGGCCTCAG  TGAAGATGTC  CTGCAAGGCT      60
TCTGGCTACA  CCTTCACTAG  CTACTGGATA  CACTGGGTAA  AACAGAGGCC  TGGACAGGGT     120
CTGGAATGGA  TTGGATACAT  TAATCCTAGT  ACTGATTATA  CTGAGTACAT  TCAGAAGTTC     180
AAGGACAAGG  CCACATTGAC  TGCAGACAAA  TCCTCCAGCA  CAGCCTACAT  GCAACTGAGC     240
AGCCTGACAT  CTGAGGACTC  TGCAGTCTAT  TACTGTGTAA  TGAAGGACTA  CTGGGGTCAA     300
GGAACTTCAG  TCACCGTCTC  CTCAGCCAAA  ACGACACCCC  CATCTGTCTA  TCCACTGGCC     360
CCTGGATCTG  CTGCCCAAAC  TAACTCCATG  GTGACCCTGG  GATGCCTGGT  CAAGGGCTAT     420
TTCCCTGAGC  CAGTGACAGT  GACCTGGAAC  TCTGGATCCC  TGTCCAGCGG  TGTGCACACC     480
TTCCCAGCTG  TCCTGCAGTC  TGACCTCTAC  ACTCTGAGCA  GCTCAGTGAC  TGTCCCCTCC     540
AGCACCTGGC  CCAGCGAGAC  CGTCACCTGC  AACGTTGCCC  ACCCGGCCAG  CAGCACCAAG     600
GTGGACAAGA  AAATTGTGCC  CAGGGATTGT  ACTAGT                                 636
```

( 2 ) INFORMATION FOR SEQ ID NO:2:

( i ) SEQUENCE CHARACTERISTICS:
        ( A ) LENGTH: 212 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Leu  Glu  Ser  Gly  Thr  Glu  Leu  Ala  Lys  Pro  Gly  Ala  Ser  Val  Lys  Met
 1              5                        10                       15

Ser  Cys  Lys  Ala  Ser  Gly  Tyr  Thr  Phe  Thr  Ser  Tyr  Trp  Ile  His  Trp
               20                       25                       30

Val  Lys  Gln  Arg  Pro  Gly  Gln  Gly  Leu  Glu  Trp  Ile  Gly  Tyr  Ile  Asn
               35                       40                       45

Pro  Ser  Thr  Asp  Tyr  Thr  Glu  Tyr  Ile  Gln  Lys  Phe  Lys  Asp  Lys  Ala
          50                       55                       60

Thr  Leu  Thr  Ala  Asp  Lys  Ser  Ser  Thr  Ala  Tyr  Met  Gln  Leu  Ser
 65                      70                       75                       80

Ser  Leu  Thr  Ser  Glu  Asp  Ser  Ala  Val  Tyr  Tyr  Cys  Val  Met  Lys  Asp
                    85                       90                       95

Tyr  Trp  Gly  Gln  Gly  Thr  Ser  Val  Thr  Val  Ser  Ser  Ala  Lys  Thr  Thr
               100                      105                      110

Pro  Pro  Ser  Val  Tyr  Pro  Leu  Ala  Pro  Gly  Ser  Ala  Ala  Gln  Thr  Asn
               115                      120                      125

Ser  Met  Val  Thr  Leu  Gly  Cys  Leu  Val  Lys  Gly  Tyr  Phe  Pro  Glu  Pro
     130                      135                      140

Val  Thr  Val  Thr  Trp  Asn  Ser  Gly  Ser  Leu  Ser  Ser  Gly  Val  His  Thr
 145                      150                      155                      160

Phe  Pro  Ala  Val  Leu  Gln  Ser  Asp  Leu  Tyr  Thr  Leu  Ser  Ser  Ser  Val
                    165                      170                      175

Thr  Val  Pro  Ser  Ser  Thr  Trp  Pro  Ser  Glu  Thr  Val  Thr  Cys  Asn  Val
               180                      185                      190

Ala  His  Pro  Ala  Ser  Ser  Thr  Lys  Val  Asp  Lys  Lys  Ile  Val  Pro  Arg
          195                      200                      205

Asp  Cys  Thr  Ser
 210
```

( 2 ) INFORMATION FOR SEQ ID NO:3:

( i ) SEQUENCE CHARACTERISTICS:
        ( A ) LENGTH: 646 bases
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
GAGCTCGTGA  TGACCCAGAC  TCCAGCAATC  ATGTCTGCAT  CTCCAGGGGA  GAAGGTCACC      60
ATGACCTGCA  GTGCCAGCTC  AAGTATAAGT  TACATGCACT  GGTACCAGCA  GAAGCCAGGC     120
ACCCCCCCCA  AAAGATGGAT  TTATGGCACA  TCCAAACTGA  CTTCTGGAGT  CCCTGCTCGC     180
TTCAGTGGCA  GTGGGTCTGG  GACCTCTTTT  TCTCTCACAA  TCAGCAGCAT  GGAGGCTGAA     240
GATGCTGCCA  CTTATTACTG  CCATCAGCGG  AGTAGTTACC  CGACGTTCGG  TGGAGGCACC     300
AAGCTGGAAA  TCAAACGGGC  TGATGCTGCA  CCAACTGTAT  CCATCTTCCC  ACCATCCAGT     360
GAGCAGTTAA  CATCTGGAGG  TGCCTCAGTC  GTGTGCTTCT  TGAACAACTT  CTACCCCAAA     420
GACATCAATG  TCAAGTGGAA  GATTGATGGC  AGTGAACGAC  AAAATGGCGT  CCTGAACAGT     480
TGGACTGATC  AGGACAGCAA  AGACAGCACC  TACAGCATGA  GCAGCACCCT  CACGTTGACC     540
AAGGACGAGT  ATGAACGACA  TAACAGCTAT  ACCTGTGAGG  CCACTCACAA  GACATCAACT     600
TCACCCATTG  TCAAGAGCTT  CAACAGGAAT  GAGTGTTAAT  TCTAGA                    646
```

( 2 ) INFORMATION FOR SEQ ID NO:4:

( i ) SEQUENCE CHARACTERISTICS:
    ( A ) LENGTH: 213 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
Glu Leu Val Met Thr Gln Thr Pro Ala Ile Met Ser Ala Ser Pro Gly
 1               5                  10                  15
Glu Lys Val Thr Met Thr Cys Ser Ala Ser Ser Ile Ser Tyr Met
            20                  25                  30
His Trp Tyr Gln Gln Lys Pro Gly Thr Pro Pro Lys Arg Trp Ile Tyr
            35                  40                  45
Gly Thr Ser Lys Leu Thr Ser Gly Val Pro Ala Arg Phe Ser Gly Ser
        50                  55                  60
Gly Ser Gly Thr Ser Phe Ser Leu Thr Ile Ser Ser Met Glu Ala Glu
65                  70                  75                  80
Asp Ala Ala Thr Tyr Tyr Cys His Gln Arg Ser Ser Tyr Pro Thr Phe
                85                  90                  95
Gly Gly Gly Thr Lys Leu Glu Ile Lys Arg Ala Asp Ala Ala Pro Thr
               100                 105                 110
Val Ser Ile Phe Pro Pro Ser Glu Gln Leu Thr Ser Gly Gly Ala
            115                 120                 125
Ser Val Val Cys Phe Leu Asn Asn Phe Tyr Pro Lys Asp Ile Asn Val
        130                 135                 140
Lys Trp Lys Ile Asp Gly Ser Glu Arg Gln Asn Gly Val Leu Asn Ser
145                 150                 155                 160
Trp Thr Asp Gln Asp Ser Lys Asp Ser Thr Tyr Ser Met Ser Ser Thr
                165                 170                 175
Leu Thr Leu Thr Lys Asp Glu Tyr Glu Arg His Asn Ser Tyr Thr Cys
                180                 185                 190
Glu Ala Thr His Lys Thr Ser Thr Ser Pro Ile Val Lys Ser Phe Asn
            195                 200                 205
Arg Asn Glu Cys Phe
    210
```

( 2 ) INFORMATION FOR SEQ ID NO:5:

( i ) SEQUENCE CHARACTERISTICS:
        ( A ) LENGTH: 666 bases
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
CTCGAGTCTG GACCTGAGCT GGTGAAGCCT GGGGGCTCAG TGACGATTTC CTGCAAAGCT      60
TCTGGCTACG GATTCACTAC CTCTTGGATG AACTGGGTGA GGCAGAGGCC TGGACAGGGT     120
CTTGAGTGGA TTGGACGGAT TTATCCTGGA AGTGGGGATA ATAATTACAA TGGGAAGTTC     180
AAGGTCAAGG CCACATTGAC TGCAGAGAGA TCCTCCACCA CAGTCTACCT GCACCTCAGC     240
AGCCTGACCT CTGTAGATTC TGCGGTCTAT TTCTGTGCAA GATTTCACTA TGATTATCGT     300
CGTTCCTATG CTATGGACTA CTGGGGTCAA GGAACTTCAG TCACCGTCTC CTCAGCCAAA     360
ACGACACCCC CATCTGTCTA TCCACTGGCC CCTGGATCTG CTGCCCAAAC TAACTCCATG     420
```

| | | | | | |
|---|---|---|---|---|---|
|GTGACCCTGG|GATGCCTGGT|CAAGGGCTAT|TTCCCTGAGC|CAGTGACAGT|GACCTGGAAC 480|
|TCTGGATCCC|TGTCCAGCGG|TGTGCACACC|TTCCCAGCTG|TCCTGCAGTC|TGACCTCTAC 540|
|ACTCTGAGCA|GCTCAGTGAC|TGTCCCCTCC|AGCACCTGGC|CCAGCGAGAC|CGTCACCTGC 600|
|AACGTTGCCC|ACCCGGCCAG|CAGCACCAAG|GTGGACAAGA|AAATTGTGCC|CAGGGATTGT 660|
|ACTAGT| | | | |666|

( 2 ) INFORMATION FOR SEQ ID NO:6:

( i ) SEQUENCE CHARACTERISTICS:
        ( A ) LENGTH: 222 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Leu Glu Ser Gly Pro Glu Leu Val Lys Pro Gly Gly Ser Val Thr Ile
 1               5                  10                  15
Ser Cys Lys Ala Ser Gly Tyr Gly Phe Thr Thr Ser Trp Met Asn Trp
                20                  25                  30
Val Arg Gln Arg Pro Gly Gln Gly Leu Glu Trp Ile Gly Arg Ile Tyr
                35                  40                  45
Pro Gly Ser Gly Asp Asn Asn Tyr Asn Gly Lys Phe Lys Val Lys Ala
        50                  55                  60
Thr Leu Thr Ala Glu Arg Ser Ser Thr Thr Val Tyr Leu His Leu Ser
 65                 70                  75                  80
Ser Leu Thr Ser Val Asp Ser Ala Val Tyr Phe Cys Ala Arg Phe His
                85                  90                  95
Tyr Asp Tyr Arg Arg Ser Tyr Ala Met Asp Tyr Trp Gly Gln Gly Thr
                100                 105                 110
Ser Val Thr Val Ser Ser Ala Lys Thr Thr Pro Pro Ser Val Tyr Pro
                115                 120                 125
Leu Ala Pro Gly Ser Ala Ala Gln Thr Asn Ser Met Val Thr Leu Gly
        130                 135                 140
Cys Leu Val Lys Gly Tyr Phe Pro Glu Pro Val Thr Val Thr Trp Asn
145                 150                 155                 160
Ser Gly Ser Leu Ser Ser Gly Val His Thr Phe Pro Ala Val Leu Gln
                165                 170                 175
Ser Asp Leu Tyr Thr Leu Ser Ser Ser Val Thr Val Pro Ser Ser Thr
                180                 185                 190
Trp Pro Ser Glu Thr Val Thr Cys Asn Val Ala His Pro Ala Ser Ser
                195                 200                 205
Thr Lys Val Asp Lys Lys Ile Val Pro Arg Asp Cys Thr Ser
        210                 215                 220
```

( 2 ) INFORMATION FOR SEQ ID NO:7:

( i ) SEQUENCE CHARACTERISTICS:
        ( A ) LENGTH: 652 bases
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

GAGCTCGTGA TGACCCAGAC TCCATCTTCC ATGTATGCAT CTCTAGGAGA GAGAGTCACT     60

-continued

| | | | | | |
|---|---|---|---|---|---|
| ATCACTTGCA | AGGCGAGTCA | GGACATTAAT | ATCTATTTAA | GTTGGTTCCA | GCAGAAACCA | 120
| GGGAAATCTC | CTAAGGCCCT | GATCTATCGT | ACAAACGGAT | TGGTAGATGG | GGTCCCATCA | 180
| AGGTTCAGTG | GCAGTGGATC | TGGGCAAGAT | TATTCTCTCA | CCATCAGCAG | CCTGGAATAT | 240
| GAAGATATGG | GAATTTATTA | TTGTCTACAG | TATGATGAGT | TTCCGTACAC | GTTCGGAGGG | 300
| GGGACCAAGC | TGGAAATAAA | ACGGGCTGAT | GCTGCACCAA | CTGTATCCAT | CTTCCACCA | 360
| TCCAGTGAGC | AGTTAACATC | TGGAGGTGCC | TCAGTCGTGT | GCTTCTTGAA | CAACTTCTAC | 420
| CCCAAAGACA | TCAATGTCAA | GTGGAAGATT | GATGGCAGTG | AACGACAAAA | TGGCGTCCTG | 480
| AACAGTTGGA | CTGATCAGGA | CAGCAAAGAC | AGCACCTACA | GCATGAGCAG | CACCCTCACG | 540
| TTGACCAAGG | ACGAGTATGA | ACGACATAAC | AGCTATACCT | GTGAGGCCAC | TCACAAGACA | 600
| TCAACTTCAC | CCATTGTCAA | GAGCTTCAAC | AGGAATGAGT | GTTAATTCTA GA | | 652

(2) INFORMATION FOR SEQ ID NO:8:

(i) SEQUENCE CHARACTERISTICS:
    (A) LENGTH: 215 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

```
Glu Leu Val Met Thr Gln Thr Pro Ser Ser Met Tyr Ala Ser Leu Gly
 1               5                  10                  15
Glu Arg Val Thr Ile Thr Cys Lys Ala Ser Gln Asp Ile Asn Ile Tyr
                20                  25                  30
Leu Ser Trp Phe Gln Gln Lys Pro Gly Lys Ser Pro Lys Ala Leu Ile
            35                  40                  45
Tyr Arg Thr Asn Gly Leu Val Asp Gly Val Pro Ser Arg Phe Ser Gly
50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Tyr
                    85                  90                  95
Thr Phe Gly Gly Gly Thr Lys Leu Glu Ile Lys Arg Ala Asp Ala Ala
                100                 105                 110
Pro Thr Val Ser Ile Phe Pro Pro Ser Ser Glu Gln Leu Thr Ser Gly
            115                 120                 125
Gly Ala Ser Val Val Cys Phe Leu Asn Asn Phe Tyr Pro Lys Asp Ile
        130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                    165                 170                 175
Ser Thr Leu Thr Leu Thr Lys Asp Glu Tyr Glu Arg His Asn Ser Tyr
                180                 185                 190
Thr Cys Glu Ala Thr His Lys Thr Ser Thr Ser Pro Ile Val Lys Ser
            195                 200                 205
Phe Asn Arg Asn Glu Cys Phe
        210                 215
```

CATALYTIC ANTIBODIES ENANTIOSELECTIVELY HYDROLYSING AMINO ACID ESTER DERIVATIVES

BACKGROUND OF THE INVENTION

1. Field of the Invention

The present invention belongs to the field of the art synthesizing optically active amino acids. Specifically, the present invention relates to a process for conducting enantioselective hydrolysis by utilizing catalytic antibodies. More specifically, the invention relates to processes for enantioselectively hydrolyzing amino acid ester derivatives with catalytic antibodies to effect optical resolution of racemic mixture of amino acid derivatives and to prepare optically active amino acids. Because the present invention allows very easy production of optically active amino acids having various substituted groups, it can contribute to basic studies on the function of living bodies, development of a novel medical drug containing optically active amino acids as an essential component, and development of methodologies for synthesizing various optically and physiologically active substances or functional compounds, which methodologies use optically active amino acids in synthesizing processes.

2. Description of the Related Art

Proteins, a primary component of the living body, are constructed with optically active amino acids, which makes a chiral environment in the living body. Therefore, many of the physiologically active substances including medical drugs are optically active substances, and it is known that bioactivity is found only in either one of enantiomers, or difference in bioactivity is observed between the enantiomers. Accordingly, developing a methodology for obtaining optically active substances is one of the targets of investigations.

The simplest process usually performed to obtain an optically active amino acid derivatives is optical resolution of racemic mixture of amino acid derivatives. The process for optical resolution includes a process employing an enzyme (e.g. a kinetic optical resolution using aminoacylase, lipase and the like) and a process forming a diastereomer, or the like. However, most suitable process must be selected depending on a particular amino acid to be resolved, because there is no common process effective for all the amino acids having a variety of substituted groups.

In such a situation as mentioned above, the inventors of the present invention have succeeded in developing a process for performing optical resolution of racemic mixture of amino acid derivatives, using catalytic antibodies, which is applicable for any amino acids. Although reactions using catalytic antibodies usually have drawbacks in that the catalytic antibodies have substrate specificity, and therefore, they have only limited applicablity, the present inventors have overcome such drawbacks by developing catalytic antibodies which enantioselectively hydrolyze ester derivatives of racemic mixture of any amino acid derivatives to produce corresponding optically active amino acids.

SUMMARY OF THE INVENTION

The present invention relates to a process for performing optical resolution of recemic body of amino acids, characterized by using catalytic antibodies enantioselectively hydrolyzing amino acid ester derivatives.

In another aspect, the present invention relates to a process for preparing optically active amino acids from racemic mixture of amino acid derivatives, characterized by using catalytic antibodies to enantioselectively hydrolyze amino acid ester derivatives.

The processes of the invention can be applied to the synthesis of both L- and D-isomers of amino acids and include two processes each consisting of the following two steps:

(1) preparing ester derivatives of racemic mixture of amino acid derivatives, and then (2) enatioselectively hydrolyzing only L-form of amino acids ester derivatives; and (1) preparing ester derivatives of racemic mixture of amino acid derivatives, and then (2) enatioselectively hydrolyzing only D-form of amino acids ester derivatives.

The catalytic antibodies as used herein are typically prepared by immunizing a mammal with, as a hapten, a compound having of the formula 3 below:

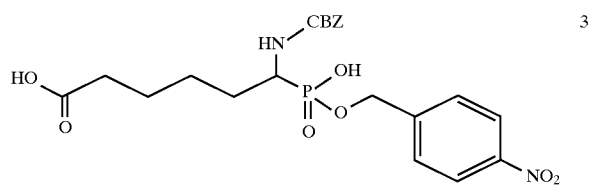

wherein CBZ is benzyloxycarbonyl.

Although CBZ in formula 3 is an amino-protecting group, other conventional amino-protecting groups known to those skilled in the art, for example, trichloroacetyl, benzyl, t-butoxycarbonyl, 9-fluorenylmethoxycarbonyl, or CBZ having a substituent such as lower alkyl, lower alkoxy, halogen, nitro, etc. in the phenyl moiety can also be used instead of CBZ. The compound of the above formula 3 has a 4-nitrobenzyl ester moiety. However, the benzyl ester moiety can have one or two substituents selected from lower alkyl, lower alkoxy, nitro, halogen, or the like in the phenyl moiety. Catalytic antibodies obtained using the haptens having substituted benzyl moiety can also hydrolyze any corresponding amino acid ester derivatives. Thus, these are also potential haptens.

In one embodiment, the invention aims at antibodies which catalyze enantioselective hydrolysis of L- and D-isomers of N-benzyloxycarbonyl amino acid ester derivatives. N-benzyloxycarbonyl amino acid is an N-protecting amino acid often used for the synthesis of peptides. Such antibodies catalyze hydrolytic reaction as shown in the following Scheme 1. Although the following explanation concerns the catalytic antibodies which are obtained by the use of the compound of the above Formula 3, those skilled in the art will understand that the following explanation is also applicable to catalytic antibodies obtained from the potential haptens mentioned above.

Scheme 1

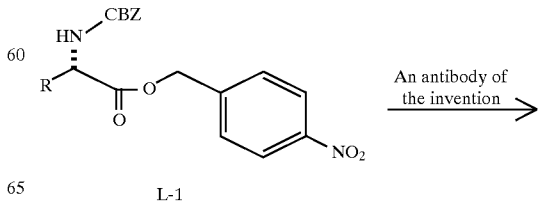

Scheme 1 (continued)

L-2

D-1

D-2 wherein CBZ is N-benzyloxycarbonyl and

R may be substantially any substituent, and, it is typically alkyl or phenyl group which is optionally substituted with hydroxy, amino, alkylthio, acyloxy or phenyl, and in more particular, $CH_3-$, $phCH_2-$, $(CH_3)_2CHCH_2-$, $CH_3(CH_2)_3-$, $CH_3SCH_2CH_2-$, $(CH_3)_2CH-ph-$, or $4-HOph-$;

wherein ph- is phenyl group;

alkyl is typically straight or branched $C_1-C_{10}$ alkyl; and acyloxy is a group of the formula: RCOO— wherein R is alkyl.

DETAILED DESCRIPTION OF THE INVENTION

The above-noted antibodies are prepared by using a known technique for catalytic antibodies reported by Lerner, R. A. et al., Science, 252, 659, 1991. Thus, the antibodies of the invention are produced by immunizing mammals using, as a hapten, the phosphonate derivative of the following formula 3 which is a transition state analog during hydrolysis.

3

Preparation of Hapten

The above phosphonate derivative can be synthesized, for example, according to the synthetic route shown in the following Scheme 2.

Scheme 2

4

5

6

3

7

8 (X = KLH)

Commercially available ethyl 6-hydroxy hexanoate is oxidized with PDC (pyridinium dichromate), the resultant compound(4) is iminated with benzylamine in sutu, and reacted with triethylphosphite to give compound (5). Compound (5) is then debenzylated by catalytic hydrogenation, and the amino group is subsequently benzyloxycarbonylated. After diethylphosphonate is deethylated by bromotrimethylsilane, the resultant phosphonic acid is reacted with 4-nitrobenzyl alcohol in the presence of DCC (dicyclohexylcarbodiimide) and 1H-tetrazole to obtain compound (6). An ethyl ester of compound (6) is alkali-hydrolyzed to obtain hapten (3). Hapten (3) is converted to activated ester (7) with hydroxysuccinimide and the latter is reacted with KLH (Keyhole limpet hemocyanin) to obtain antigen (8).

Preparation of Catalytic Antibodies

BALB/c mice are immunized with the above antigen (8) to give monoclonal antibodies.

A BALB/c mouse (female, 4-week old) is immunized four times with antigen (8), and spleen cells are removed. After cell fusion is performed in conventional manner, resultant hybridomas are screened using Enzyme-Linked Immuno Sorbent Assay (ELISA) to obtain a hybridoma producing antibodies which bind to the hapten.

Repeated clonings by limiting dilution are performed to obtain a monoclonal IgG-producing hybridoma. Crude antibodies precipitated by adding $(NH_4)_2SO_4$ to the supernatant of the culture are purified using cation exchange chromatography and protein G affinity chromatography.

Identification of Catalytic Antibodies

The above-obtained antibodies are screened for catalytic activity thereof. In order to simply and quickly conduct the screening of the catalytic activity, the esters (L-10) and (D-10) shown in the following Scheme 3 are used as substrates, which allow to trace the progress of hydrolysis by measuring the changes in fluorescence intensity. Fluorescence due to anthranilic acid moiety in the esters (L-10) and (D-10) is quenched by 4-nitrobenzyl group existing in the molecules, and when the quenching is dissolved by hydrolysis, fluorescence intensity thereof increases. Namely, the esters (L-11) and (D-11) in the following Scheme 3 are fluorogenic substances.

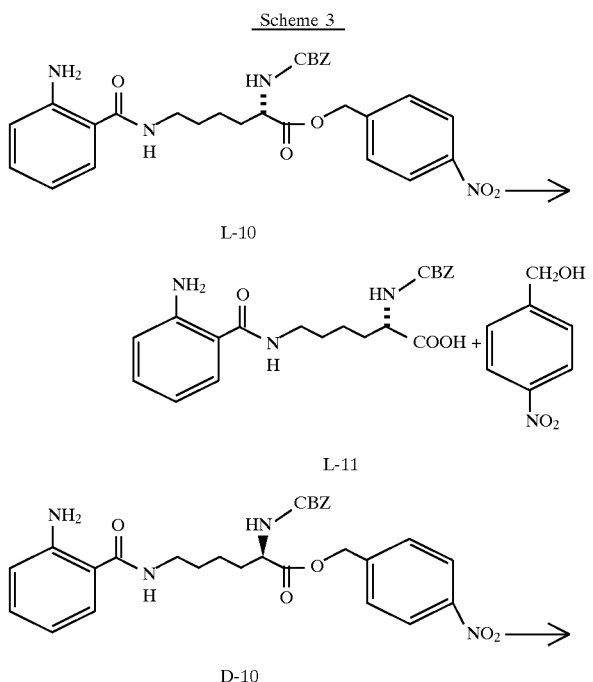

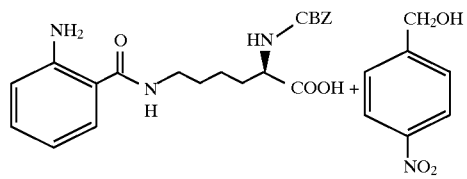

D-11

Ester (L-10) is equivalently mixed with ester (D-10) to prepare a fluorogenic substrate (DL-10) and the fluorogenic substrate is used in the screening of the catalytic activity.

At first, changes in fluorescent intensity of the obtained purified antibodies are traced at λ ex 340 nm and λ em 415 nm for 10 minutes using the fluorogenic substrate (DL-10). By performing the screening, antibodies hydrolyzing the fluorogenic substrate are identified. Next, the similar procedure is performed by using either one of the fluorogenic substrates (L-10) and (D-10) to evaluate enantioselectivity of each antibody.

PROCEDURE AND EFFECT OF THE INVENTION

The antibodies having selective catalytic activities to L- or D-form, as obtained above, are examined for their substrate-specificity and enantioselectivity to various amino acid ester derivatives by HPLC analysis.

Antibody 7G12 (see working Examples hereinafter described) having selective catalytic activity to L-form catalyzed the hydrolysis of L-form (L-1) of substrates derived from alanine, phenylalanine, leucine, norleucine, methionine, valine, phenylglycine, 4-hydrophenylglycine, and lysine, but the antibody 7G12 did not catalyze the hydrolysis of the corresponding D-form substrates (D-1). Namely, the antibody 7G12 enantioselectively catalyzed the hydrolysis of various substrates.

Antibody 3G2 (see working Examples hereinafter described) having selective catalytic activity to D-form catalyzed the hydrolysis of D-form (D-1) of substrates derived from alanine, phenylalanine, leucine, norleucine, methionine, valine, phenylglycine, and 4-hydrophenylglycine, but the antibody 3G2 did not catalyze the hydrolysis of the corresponding L-form substrates (L-1). Thus, the antibody 3G2 enantioselectively catalyzed the hydrolysis of various substrates.

The above results demonstrated that the antibodies of the invention obtained by the use of the phosphonate (3) as a hapten enantioselectively catalyze the hydrolysis of various amino acid ester derivatives.

The reason why the antibodies of the invention show such non-specificity to substrates in spite of being antibodies is considered as follows. It is known that the total maximum contacting surface area between hapten and antibody is 700–800 Å$^2$, and that the contacting surface area between low molecular hapten (M.W. up to 350) and antibody is 250–400 Å$^2$. This means that the recognition site of antibody has such size, and it is presumed that, when an antibody derived from the above hapten 3 recognizes CBZ group, 4-nitrobenzyl alcohol, phosphonate, and stereochemistry of α-position of the hapten 3, recognition site of the antibody is sufficiently filled by them, and substituent (R) on α-position of the hapten gets out of the recognition site. Thus, when the antibodies of the invention catalyze the hydrolysis of amino acid ester derivatives, α-substituent (R) thereof will be outside the recognized site, and therefore, it is believed that the antibodies catalyze every substrate irrespective of their substituents (R) so long as said substrates have the same stereochemistry as the enantiomer of the hapten recognized by the antibodies.

Antibodies 7G12 and 3G2 catalyzed indeed the enantioselective hydrolysis of wide range of substrates according to the above-noted design (see working Examinations hereinafter described). Accordingly, it was demonstrated that the immunization by the use of hapten having a structural unit which has a size corresponding to that of the recognition site of the antibodies, and a structural unit which may be protruded outside said recognition site gave the catalytic antibodies the capability of performing the stereospecific reaction and catalyzing the wide range of substrates thanks to their high recognition abilities.

As mentioned above, the antibodies of the invention can be utilized in a process for preparing optically active amino acid derivatives from their racemic mixture. Specifically, such process for preparing an optically active amino acid comprising the steps of:

a) subjecting a racemic mixture of an amino acid derivatives to an ester-forming reaction;

b) selectively hydrolyzing a desired stereoisomer, D- or L-isomer, of the ester derivative by the use of a catalytic antibody which enantioselectively hydrolyzes an amino acid ester derivative; and c) treating the resultant reaction mixture in conventional manner, for example, making the mixture acidic or basic and then extracting with an organic solvent to leave an aqueous layer, from which the desired hydrolyzed stereoisomer is isolated.

The present invention will be illustrated in more detail with reference to the following Examples and Examinations. However, none of them intends to limit the scope of the invention.

EXAMPLE 1

Synthesis of hapten (3)

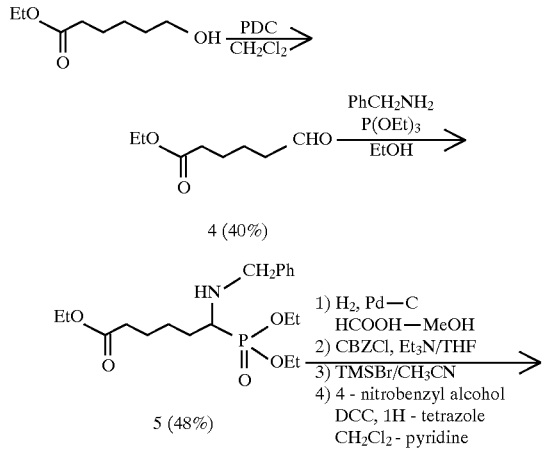

-continued
Synthesis of hapten (3)

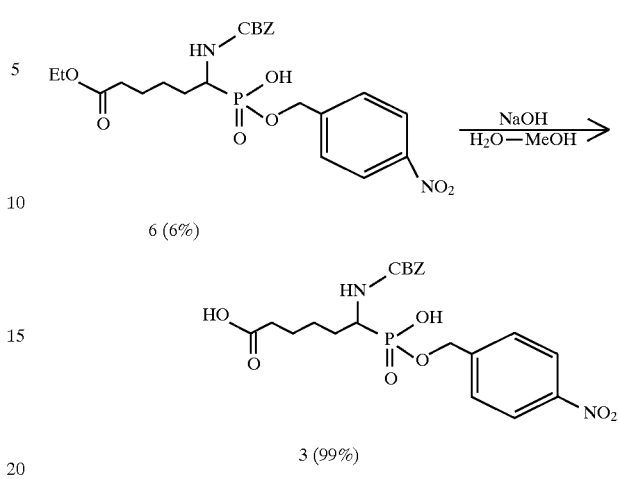

1. Synthesis of Compound (4)

To a solution of commercially available ethyl 6-hydroxyhexanoate (2.83 g, 17.7 mmol) in methylene chloride (70 ml) was added PDC (pyridinium dichromate) (9,95 g, 26.4 mmol) at room temperature. After stirring for 5 hours, the reaction mixture was purified by flash column chromatography over silica gel, eluting with ethyl acetate/hexane (1:2), to obtain compound (4) (1.1276 g, 40%).

$^1$H-NMR (500 MHz, CDCl$_3$): δ9.78 (t, J=1.4 Hz, 1H), 4.14 (q, J=7.2 Hz, 2H), 2.50–2.46 (m, 2H), 2.37–2.30 (m, 2H), 1.71–1.63 (m, 4H), 1.26 (t, J=7.2, 3H).

2. Synthesis of Compound (5)

To a solution of compound (4) (1.1276 g, 7.13 mmol) in ethanol (2.5 mL) were added benzylamine (1.56 ml, 14.3 mmol) and triethylphosphite (2.44 mL, 14.2 mmol) at room temperature. The mixture was stirred at room temperature for 17.5 hours and then at 40° C. for 6 hours. After the solvent was evaporated, the residue was purified by flash column chromatography over silica gel, eluting with ethyl acetate/isopropanol (20:1), to obtain compound (5) (1.1276 g, 40%).

$^1$H-NMR (500 MHz, CDCl$_3$): δ7.35–7.23 (m,5H), 4.21–4.09 (m,6H), 3.97 (d, J=13.1 Hz, 2H), 3.88 (dd, J=13.1 Hz, 1.3 Hz, 2H), 2.85 (m, 1H), 2.30–2.25 (m, 2H), 1.83–1.53 (m, 6H), 1.34 (t, J=7.0 Hz, 6H), 1.25 (t, J=7.1 Hz, 3H).

FBMAS (fast atom bombardment mass) m/z: 386 (M+$_+$N). HR-FABMAS (high resolution-FABMAS) for C$_{19}$H$_{33}$O$_5$NP(M+$_+$H): Calcd.: 386.2132, Found: 386.2092.

3. Synthesis of compound (6)

To a solution of compound (5) (473.0 mg, 1.23 mmol) in methanol (3.0 mL) and formic acid (0.40 mL) was added 10% Pb-C (4.6 mg), and the mixture was stirred at room temperature for 2.5 days under hydrogen. The reaction mixture was filtered and the filtrate was concentrated under reduced pressure to obtain a colorless residue. The residue was dissolved in THF (5.0 mL), and carbobenzoxy chloride (700 μL, 4.90 mmol) and triethyl amine (1.71 mL, 12.3 mmol) were added thereto at room temperature. After stirring for 3 hours, 1N hydrochloric acid was added, and the mixture was extracted with ethyl acetate. The combined organic phase was washed with saturated brine, dried, and evaporated. The residue was purified by flush column chromatography over silica gel, eluting with ethyl acetate to obtain colorless gum (120.5 mg).

The gum (120.5 mg) was dissolved in methylene chloride (0.5 mL) and bromotrimethylsilane (222 μL, 1.68 mmol) was added thereto at room temperature. After stirring at 35°

C. for 2 hours, the solvent was evaporated off, and to the residue were added acetonitrile (1.0 mL) and water (0.2 mL). After 12 hours, the solvent was evaporated and the residue was dried. To a solution of the residue in methylene chloride (1.0 mL) and pyridine (0.5 mL) were added 4-nitrobenzyl alcohol (61.2 mg, 0.40 mmol), 1H-tetrazole (9.7 mg, 0.14 mmol) and DCC (261.5 mg, 1.27 mmol), and the mixture was stirred at 35° C. for 5 hours. After the solvent was evaporated off, acetonitrile was added to the residue, and the mixture was filtered. The filtrate was purified by HPLC (YMCA-323: C-18, 10 mm in diameter× 250 mm in length, acetonitrile/0.1% aqueous trifluoroacetic acid solution=50/50, 3.0 ml/min, 254 nm) to obtain compound (6) (34.5 mg, 6% from compound (5)).

$^1$H-NMR (500 MHz, CDCl$_3$): δ8.22 (d, J=8.6 Hz, 2H), 7.62 (d, J=8.6 Hz, 2H), 7.38–7.28 (m, 5H), 5.18 (ABX, J$_{AB}$=13.5Hz, J$_{AX}$=J$_{BX}$=7.4 HZ, Δυ=16.2 Hz, 2H), 5.11 (AB, J=12.6 Hz, Δυ=20.2 Hz, 2H), 4.14 (q, J=7.1 Hz, 2H), 4.06 (m,1H), 2.33 (t, J=7.3 Hz, 2H), 1.95–1.37 (m, 6H), 1.27 (t, J=7.1 Hz, 3H).

FABMAS m/z: 509 (M+$_+$H). HR-FABMAS for C$_{23}$H$_{30}$O$_9$N$_2$P(M+$_+$H): Calcd.: 509.1689, Found: 509.1688.

4. Synthesis of compound (3)

To a solution of compound (6) (15.0 mg, 0.0295 mmol) in methanol (0.2 mL) and water (0.2 mL) was added 1N NaOH (0.1 mL, 0.1 mmol) at room temperature. After 6.5 hours, the reaction mixture was made acidic by addition of trifluoroacetic acid, and the mixture was purified by HPLC (YMCA-323: C-18, 10 mm in diameter×250 mm in length, acetonitrile/0.1% aqueous trifluoroacetic acid solution=50/50, 254 nm) to obtain compound (3) (14.0 mg, 99%).

$^1$H-NMR (500 MHz, CD$_3$OD): δ8.22 (d, J=8.6 Hz, 2H), 7.61 (d, J=8.6 Hz, 2H), 7.37–7.28 (m, 5H), 5.18 (ABX, J$_{AB}$=13.5 Hz, J$_{AX}$=J$_{BX}$=7.4 HZ, Δυ=16.7 Hz, 2H), 5.11 (AB, J=12.5 Hz, Δυ=26.6 Hz, 2H), 4.07 (m,1H), 2.32 (t, J=7.3 Hz, 2H), 1.97–1.38 (m, 6H).

FABMAS m/z: 503 (M+$_+$Na), 481 (M+$_+$H). HR-FABMAS for C$_{21}$H$_{25}$O$_9$N$_2$PNa(M+$_+$Na): Calcd.: 503.1196, Found: 503.1202.

EXAMPLE 2

Condensation of hapten and carrier proteins

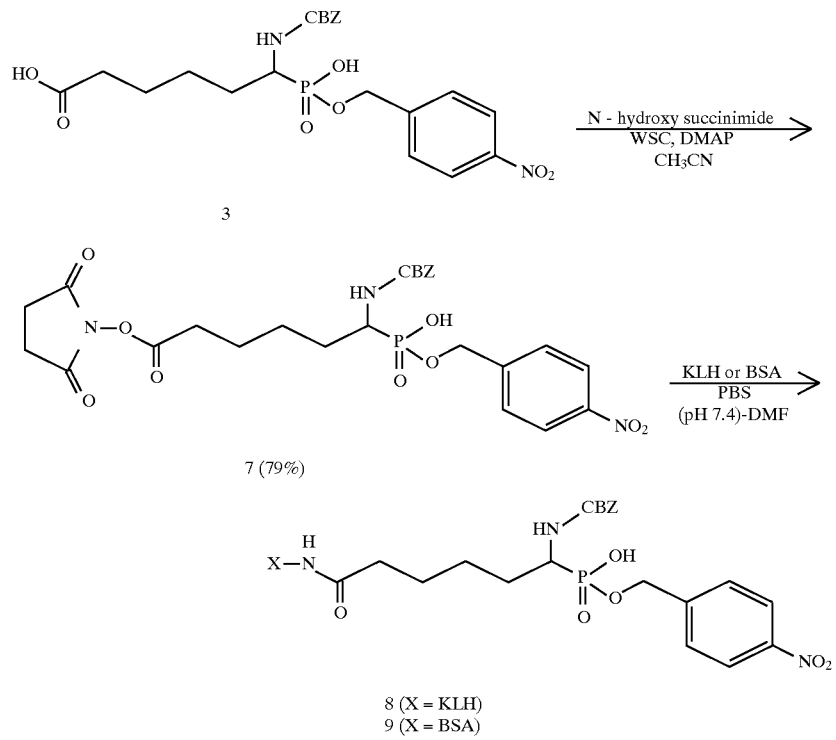

5. Synthesis of compound (7)

To a solution of compound (3) (6.4 mg, 0.013 mmol) in acetonitrile (0.3 mL) were added N-hydroxysuccinimide (2.5 mg, 0.022 mmol), WSC water-soluble carbodiimide (WSC) (8.3 mg, 0.04:3 mmol) and dimethylaminopyridine (DMAP) (0.1 mg, 0.0008 mmol) and the mixture was stirred for 2 hours. The reaction mixture was purified by HPLC (YMCA-323: C-18, 10 mm in diameter × 250 mm in length, acetonitrile/0.1% aqueous trifluoroacetic acid solution=50/50, 3.0 mL/min, 254 nm) to obtain compound (7) (6.1 mg, 79%).

$^1$H-NMR (500 MHz, CD$_3$OD): δ8.23 (d, J=8.7 Hz, 2H), 7.62 (d, J=8.7 Hz, 2H), 7.38–7.27 (m, 1H), 5.19 (ABX, J$_{AB}$=13.4 Hz, J$_{AX}$=J$_{BX}$=7.5 HZ, Δυ=15.9 Hz, 2H), 5.11 (AB, J=12.5 Hz, Δυ=16.4 Hz, 2H), 4.08 (m,1H), 2.85 (s, 4H), 2.66 (t, J=7.2 Hz, 2H), 1.97–1.43 (m, 6H).

6. Synthesis of KLH-condensate (8)

To a solution of compound (7) (2.5 mg, 0.0043 mmol) in DMF (60 μL)-200 mM Na$_2$HPO$_4$-NaH$_2$PO$_4$, pH7.4 (0.5 mL) was added a solution of KLH in 10 mM NaH$_2$PO$_4$, pH 7.4 (11.3 mg/mL, 442 μL). After 21 hours, the reaction mixture was purified by Sephadex G-25M (Pharmacia, PD-10), eluting with PBS, to obtain KLH-condensate (8). The concentration of the protein therein was determined by Bradford's method (1.3 mg/mL).

7. Synthesis of BSA-condensate (9)

To a solution of compound (7) (3.0 mg, 0.0052 mmol) in DMF (40 μL) was added a solution of BSA (6.0 mg) in 200 mM Na₂HPO₄-NaH₂PO₄, pH 7.4 (0.5 mL) at room temperature. After 12 hours, the reaction mixture was purified by Sephadex G-25M (Pharmacia, PD-10), eluting with PBS, to obtain KLH-condensate (9). The concentration of the protein therein was determined according to Bradford's method (1.3 mg/mL). The compound (9) was used for ELISA analysis.

EXAMPLE 3

Immunization

A solution of 50 μg of the antigen (KLH-condensate), prepared in Example 2, in 50 μL of saline was mixed with an equal amount of Freund's complete adjuvant, and the mixture was intraperitoneally injected to BALB/c mice (4-week old, female). After 10 days, the mice were boostered with a mixture of the antigen-saline solution (50 μg/50 μL) and equal amount of Freund's incomplete adjuvant and, following 10 days, boostered again with the same mixture. After 7 days, blood was taken from the tail vein of the mouse. Antibody titer was assayed using BSA-condensate by ELISA, which uses as a secondary antibody, biotinized anti-mouse IgG antibodies, avidin, and biotinized peroxidase, and the titer measured 2.5×10⁵. One month after the second booster, the antigen-saline solution (100 μg/100 μL) was administered via the tail vein (final immunization).

EXAMPLE 4

Preparation of Hybridoma

Three days after the final immunization, the spleen of the mouse was removed, followed by cell fusion of 1.9×10⁸ spleen cells and 2.7×10⁷ myeloma cells (×63/Ag 8.653) using polyethyleneglycol. Using ten 96-well plates each containing HAT selection medium (RPMI medium containing 0.1 mM hypoxanthine, 0.4 μM aminopterin, 0.016 mM thymidine, and 10% fetus bovine serum) containing 6×10⁵ feeder cells (mouse thymocytes)/well, selection of the hybridomas obtained was conducted (at 37° C., under 10% CO₂). Following 8–14 days, supernatants removed from the wells in which a growth of a colony was found were subjected to screening by ELISA. Out of positive 111 wells, 57 wells were subjected to cloning to obtain 39 clones. ELISA analysis using anti-mouse IgG H-chain antibody demonstrated that all of the 39 clones produced IgG.

EXAMPLE 5

Preparation of Monoclonal Antibodies

Each of 39 hybridomas prepared in Example 4 was cultured in a complete medium (RPMI medium containing 10% fetus bovine serum) for about 7 days. The supernatants were precipitated with equal volume of aqueous saturated ammonium sulfate solution and then subjected to cation exchange chromatography on a S-Sepharose column and affinity chromatography on a protein G column to obtain 10–20 mg of the purified antibodies.

PREPARATION 1

Synthesis of fluorogenic substrate (L-10)

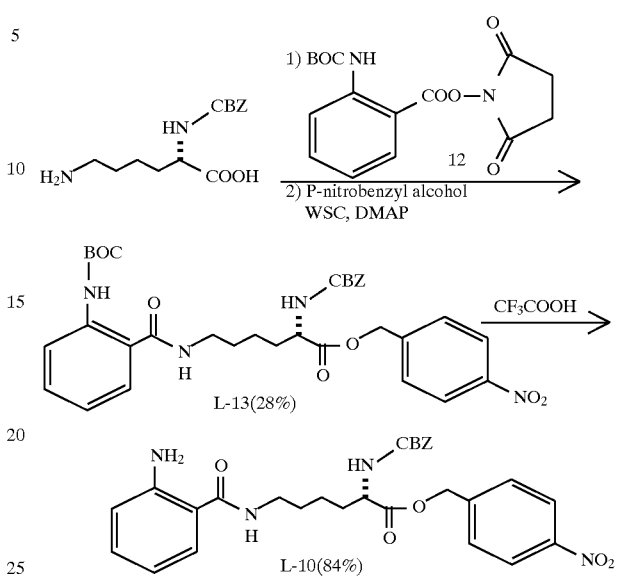

1. Synthesis of compound (12)

To a solution of commercially available anthranilic acid (1.3737 g, 10.0 mmol) in 0.5N sodium hydroxide (20.0 mL), dioxane (10.0 mL) and acetonitrile (2.0 mL) was added di-t-butyldicarbonate (3.124 g, 14.3 mmol) at 0° C. Following 8-hour stirring at room temperature, volatile solvent was evaporated under reduced pressure. To the reaction mixture were added ice and 10% citric acid solution and the mixture was extracted with ethyl acetate. The combined organic phase was washed with saturated brine and dried. The solvent was evaporated, and the residue was crystallized from ethyl acetate-hexane to obtain t-butoxycarbonyl anthranilic acid (1.71 g, 72%).

¹H-NMR (500 MHz, CDCl₃): δ10.1 (s, 1H), 8.47 (d, J=8.0 Hz, 1H), 8.09 (dd, J=8.0 Hz, 1.4 Hz, 1H), 7.56 (dt, J=8.0 Hz, 1.4 Hz, 1H), 7.04 (t, J=8.0 Hz, 1H), 1.54 (s, 9H).

t-Butoxycarbonylanthranilic acid is known (Nichino, N.; Powers, J. C. J. Biol. Chem. 1980, 255, 3482). To a solution of t-butoxycarbonylanthranilic acid (378.9 mg, 1.60 mmol) in methylene chloride (2.5 mL) were added N-hydroxysuccinimide (225.9 mg, 1.96 mmol), WSC (565.9 mg, 2.95 mmol), DMAP (4.7 mg, 0.04 mmol) at room temperature, and the mixture was stirred for 1 hour. To the reaction mixture was added 1% citric acid solution and the mixture was extracted with methylene chloride. The combined organic phase was washed with saturated brine and dried. The solvent was evaporated and the residue was crystallized from ethyl acetate-hexane to give compound (12) (199.7 mg, 30%).

¹H-NMR (500 MHz, CDCl₃): δ9.49 (s, 1H), 8.51 (d, J=8.0 Hz, 1H), 8.17 (d, J=8.0 Hz,1H), 7.63 (d, J=8.0 Hz,1H), , 7.07 (d, J=8.0 Hz, 1H), 2.93 (s, 4H), 1.52 (s, 9H).

2. Synthesis of compound (L-13)

A mixture of compound (12) (67.3 mg, 0.201 mmol), Nα-benzyloxycarbonyl-L-lysine (56.4 mg, 0.201 mmol), and diisopropylethylamine (0.04 mL, 0.230 mmol) was stirred in DMF (0.2 mL), methanol (0.2 mL), ethyl acetate (0.1 mL) and water (0.1 mL) at room temperature for 16 hours. Volatile solvent was evaporated under reduced pressure and the residue was purified by silica gel flush column chromatography, eluting with ethyl acetate/isopropanol/ water (9:1:0—8:2:0.2—5:3:1) to give the residue (122.2 mg). To a solution of the residue (122.2 mg) in methylene chloride (1.0 mL) and acetonitrile (0.1 mL) were added 4-nitrobenzylalcohol (34.9 mg, 0.228 mmol), WSC (58.6 mg, 0.306 mmol) and DMAP (1.4 mg, 0.011 mmol) at room temperature and stirred for 4 hours. The reaction mixture was purified by silica gel flush column chromatography, eluting with ethyl acetate/hexane (1:1.1), to give compound (L-13) (35.7 mg, 28% from compound (12)).

$^1$H-NMR (600 MHz, CDCl$_3$): δ10.1 (s, 1H), 8.33 (d, J=8.0 Hz, 1H), 8.20 (d, J=8.0 Hz, 2H), 7.52 (d, J=8.0 Hz, 2H), 7.44–7.38 (m, 2H), 7.35–7.28 (m, 5H), 6.95 (t, J=8.0 Hz, 1H), 6.37 (brs, 1H), 5.36 (brs, 1H), 5.24 (AB, J=13.3 Hz, Δυ=16.6 Hz, 2H), 5.06 (AB, J=12.3 Hz, Δυ=36.0 Hz, 2H), 4.46 (m, 1H), 3.43–3.37 (m, 2H), 1.95–1.40 (m, 6H).

3. Synthesis of compound (L-10)

To a solution of compound (L-13) (54.1 mg, 0.0858 mmol) in methylene chloride (0.3 mL) was added trifluoroacetic acid (0.2 mL) at room temperature and stirred for 1 hour. The solvent was evaporated under reduced pressure and purified by HPLC (YMCA-323: C-18, 10 mm in diameter×250 mm in length, acetonitrile/0.1% aqueous trifluoroacetic acid solution=60/40, 3.0 mL/min, 254 nm) to obtain compound (L-10) (38.1 mg, 84%). The compound (L-10) was crystallized from ethyl acetate-hexane.

$^1$H-NMR (600 MHz, CDCl$_3$-CD$_3$OD): δ8.21 (d, J=8.0 Hz, 2H), 7.49 (d, J=8.0 Hz, 2H), 7.37–7.25 (m, 6H), 7.19 (t, J=8.0 Hz, 1H), 6.65 (d, J=8.0 Hz, 1H), 6.64 (t, J=8.0 Hz, 1H), 5.25 (AB, J=13.3 Hz, 2H), 5.08 (AB, J=12.3 Hz, Δυ=24.6 Hz, 2H), 4.40 (m,1H), 3.42–3.34 (m, 2H), 1.94–1.85 (m,1H), 1.80–1.72 (m,1H), 1.68–1.54 (m, 2H), 1.51–1.39 (m, 2H).

PREPARATION 2

Synthesis of Fluorogenic Substrate (D-10)

The ester (D-10) was prepared according to the same procedure as that described in Preparation 1, except for using D-form of Nα-benzyloxycarbonyl-D-lysine.

Physico-chemical properties: $^1$H-NMR spectrum of D-10 was the same as that of L-10.

PREPARATION 3

Synthesis of substrate compounds (L-1) and (D-1)

Method A

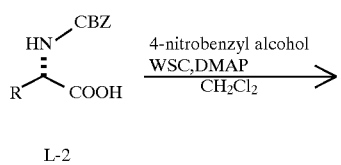

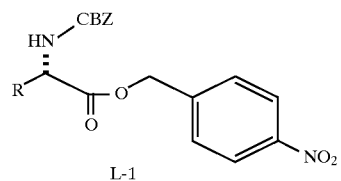

-continued
Synthesis of substrate compounds (L-1) and (D-1)

Method B

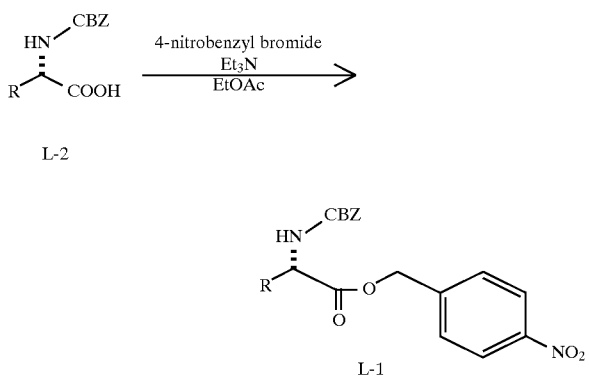

General synthesis of compounds (L-1) and (D-1)

According to the following methods A and B, various amino acid ester derivatives were synthesized.

Method A: A solution of commercially available L- or D-carbobenzoxy amino acid (1 eq.), 4-nitrobenzylalcohol (1.1 eq.), WSC (1.3–1.6 eq.), and DMAP (0.01 eq.) in methylene chloride was stirred at room temperature for 1 hour. The solvent was evaporated under reduced pressure, and ice and 1N hydrochloric acid were added to the resultant residue, and the mixture was extracted with ethyl acetate. The combined organic phase was washed with saturated brine and dried. The solvent was evaporated, and the residue was purified by silica gel flush column chromatography to obtain compound (L-1) or (D-1).

Method B: A solution of commercially available L- or D-carbobenzoxy amino acid (1 eq.), 4-nitrobenzylbromide (1.5 eq.), and triethylamine (1.5 eq.) in ethyl acetate was heated under reflux for 2 hours. The reaction mixture was cooled, to which ice and 1N hydrochloric acid were added, and the mixture was extracted with ethyl acetate. The combined organic phase was washed with saturated brine and dried. The solvent was evaporated, and the residue was purified by silica gel flush column chromatography to obtain compound (L-1) or (D-1).

1. Synthesis of N-(benzyloxycarbonyl)alanine 4-nitrobenzyl ester (R=CH$_3$)

According to the method A, the titled compound was synthesized, purified by silica gel flush column chromatography, eluting with ethyl acetate/hexane (2:3), and crystallized from ethyl acetate-hexane.

$^1$H-NMR (500 MHz, CDCl$_3$): δ8.21 (d, J=8.0 Hz, 2H), 7.49 (d, J=8.0 Hz, 2H), 7.37–7.30 (m, 5H), 5.26 (s, 2H), 5.24 (brd, 1H), 5.12 (s, 2H), 4.47 (m, 1H), 1.45 (d, J=7.2 Hz, 3H).

FABMAS m/z: 359 (M+$_+$H). HR-FABMAS for C$_{18}$H$_{19}$O$_6$N$_2$ (M+$_+$H): Calcd.: 359.1244; Found: 359.1244.

2. Synthesis of N-(benzyloxycarbonyl)phenylalanine 4-nitrobenzyl ester (R=PhCH$_2$).

According to the method A, the titled compound was synthesized, purified by silica gel flush column chromatography, eluting with ethyl acetate/hexane (2:3), and crystallized from ethyl acetate-hexane.

$^1$H-NMR (600 MHz, CDCl$_3$): δ8.17 (d, J=8.0 Hz, 2H), 7.38–7.23 (m, 10H), 7.08 (m, 2H), 5.23 (brd, J=7.5 Hz, 1H), 5.19 (s, 2H), 5.09 (s, 1H), 4.92 (m, 1H), 3.12 (d, J=6.8 Hz, 2H).

3. Synthesis of N-(benzyloxycarbonyl)leucine 4-nitrobenzyl ester (R=(CH$_3$)$_2$CHCH$_2$).

According to the method A, the titled compound was synthesized, purified by silica gel flush column chromatography, eluting with ethyl acetate/hexane (1:2).

$^1$H-NMR (600 MHz, CDCl$_3$): δ8.22 (d, J=8.3 Hz, 2H), 7.50 (d, J=8.3 Hz, 2H), 7.40–7.30 (m, 5H), 5.25 (AB, J=13.4 Hz, Δυ=11.8 Hz, 2H), 5.11 (AB, J=11.4 Hz, Δυ=6.1 Hz, 2H), 5.13–5.11 (1H), 4.46 (m,1H), 1.74–1.52 (m, 3H), 0.95 (d, J=7.2 Hz, 3H), 0.94 (d, J=7.2 Hz, 3H).

4. Synthesis of N-(benzyloxycarbonyl)norleucine 4-nitrobenzyl ester (R=CH$_3$CH$_2$CH$_2$CH$_2$).

According to the method B, the titled compound was synthesized, purified by silica gel flush column chromatography, eluting with ethyl acetate/hexane (2:5), and crystallized from ethyl acetate-hexane.

$^1$H-NMR (500 MHz, CDCl$_3$): δ8.22 (d, J=8.5 Hz, 2H), 7.50 (d, J=8.5 Hz, 2H), 7.38–7.30 (m, 5H), 5.26 (s, 2H), 5.20 (brd, J=7.9 Hz, 1H), 5.12 (s, 2H), 4.43 (m, 1H), 1.85 (m, 1H), 1.68 (m, 1H), 1.37–1.23 (m, 4H), 0.87 (t, J=6.9 Hz, 3H).

5. Synthesis of N-(benzyloxycarbonyl)methionine 4-nitrobenzyl ester (R=CH$_3$SCH$_2$CH$_2$).

According to the method A, the titled compound was synthesized, purified by silica gel flush column chromatography, eluting with ethyl acetate/hexane (2:3).

$^1$H-NMR (600 MHz, CDCl$_3$): δ8.22 (d, J=8.0 Hz, 2H), 7.51 (d, J=8.0 Hz, 2H), 7.39–7.32 (m, 5H), 5.42 (brd, J=7.1 Hz, 1H), 5.27 (AB, J=12.9 Hz, Δυ=12.4 Hz, 2H), 5.12 (s, 2H), 4.59 (m, 1H), 2.53 (t, J=7.1 Hz, 2H), 2.19 (m, 1H), 2.07 (s, 3H), 2.01 (m, 1H).

6. Synthesis of N-(benzyloxycarbonyl)valine 4-nitrobenzyl ester (R=(CH$_3$)$_2$CH).

According to the method A, the titled compound was synthesized, purified by silica gel flush column chromatography, eluting with ethyl acetate/hexane (1:2), and crystallized from ethyl acetate-hexane.

$^1$H-NMR (500 MHz, CDCl$_3$): δ8.22 (d, J=8.5 Hz, 2H), 7.51 (d, J=8.5 Hz, 2H), 7.39–7.31 (m, 5H), 5.26 (s, 2H), 5.23 (brd, J=8.8 Hz, 1H), 5.12 (s, 2H), 4.38 (dd, J=4.8 Hz, δ.8 Hz, 1H), 2.20 (m, 1H), 0.98 (d, J=6.8 Hz, 3H), 0.88 (d, J=6.8 Hz, 3H).

7. Synthesis of N-(benzyloxycarbonyl)phenylglycine 4-nitrobenzyl ester (R=Ph).

According to the method B, the titled compound was synthesized, purified by silica gel flush column chromatography, eluting with ethyl acetate/hexane (2:5) and crystallized from ethyl acetate-hexane.

$^1$H-NMR (500 MHz, CDCl$_3$): δ8.12 (d, J=8.5 Hz, 2H), 7.39–7.30 (m, 5H), 7.27 (d, J=8.5 Hz, 2H), 5.77 (brd, J=7.1 Hz, 1H), 5.44 (d, J=7.1 Hz, 1H), 5.25 (AB, J=13.4 Hz, Δυ=27.4 Hz, 2H), 5.11 (AB, J=12.1 Hz, Δυ=19.8 Hz, 2H).

8. Synthesis of N-(benzyloxycarbonyl) 4-hydroxyphenylglycine 4-nitrobenzyl ester (R=4-HOPh).

According to the method B, the titled compound was synthesized, purified by silica gel flush column chromatography, eluting with ethyl acetate/hexane (1:1.25), and crystallized from ethyl acetate-hexane.

$^1$H-NMR (600 MHz, CDCl$_3$): δ8.14 (d, J=8.5 Hz, 2H), 7.38–7.31 (m, 5H), 7.30 (d, J=8.5 Hz, 2H), 7.22 (d, J=8.5 Hz, 2H), 6.81 (d, J=8.5 Hz, 2H), 5.70 (brd, J=7.1 Hz, 1H), 5.36 (d, J=7.1 Hz, 1H), 5.24 (AB, J=13.9 Hz, Δυ=24.2 Hz, 2H), 5.11 (AB, J=12.0 Hz, Δυ=21.1 Hz, 2H), 5.10 (s, 1H).

9. Synthesis of Nα-(benzyloxycarbonyl)-Nε-(tert-butoxycarbonyl)lysine 4-nitrobenzyl ester.

According to the method B using Nα-(benzyloxycarbonyl)-Nε-(tert-butoxycarbonyl)lysine, the titled compound was synthesized, purified by silica gel flush column chromatography, eluting with ethyl acetate/hexane (2:3), and crystallized from ethyl acetate-hexane.

$^1$H-NMR (600 MHz, CDCl$_3$): δ8.22 (d, J=8.3 Hz, 2H), 7.50 (d, J=8.3 Hz, 2H), 7.38–7.30 (m, 5H), 5.40 (brd, J=6.6 Hz, 1H), 5.25 (AB, J=12.6 Hz, Δυ=8.1 Hz, 2H), 5.11 (AB, J=12.2 Hz, Δυ=12.0 Hz, 2H), 4.55 (m, 1H), 4.41 (m, 1H), 3.12–3.07 (m, 2H), 1.88 (m, 1H), 1.72 (m, 1H), 1.60–1.31 (m, 4H), 1.42 (s, 9H).

10. Synthesis of Nα-(benzyloxycarbonyl)-D-lysine 4-nitrobenzyl ester (R=H$_2$NCH$_2$CH$_2$CH$_2$CH$_2$).

To a solution of Nα-(benzyloxycarbonyl)-Nε-(tert-butoxycarbonyl)-D-lysine 4-nitrobenzyl ester (210.5 mg, 0.408 mmol) in chloroform (1.0 mL) was added trifluoroacetic acid (0.3 mL) at room temperature and the mixture was stirred for 8 hours. The solvent was evaporated under reduced pressure and the residue was crystallized from ethyl acetate-hexane.

$^1$H-NMR (500 MHz, CDCl$_3$-CD$_3$OD): δ8.22 (d, J=8.5 Hz, 2H), 7.51 (d, J=8.5 Hz, 2H), 7.40–7.26 (m, 5H), 5.27 (AB, J=13.3 Hz, Δυ=19.9 Hz, 2H), 5.11 (AB, J=12.3 Hz, Δυ=19.1 Hz, 2H), 4.35 (m, 1H), 2.87 (t, J=7.2 Hz, 2H), 1.88 (m, 1H), 1.77–1.56 (m, 3H), 1.50–1.37 (m, 2H).

EXAMINATION 1

Identification of Monoclonal Antibodies Having Catalytic Activity

1. Identification of Monoclonal Antibodies Having Hydrolyzing Activity by Measuring Fluorescence.

To a solution of each of 39 purified antibodies, prepared in Example 5, in 50 mM Tris-buffered solution, pH 8.0 (360 μL), was added a mixture (DL-10) of equal amounts of compounds (L-10) and (D-10), which were respectively prepared in Preparations 1 and 2, in 150 μM DMSO solution (40 μL) at 25 °C., and they were mixed with stirring to obtain a reaction mixture containing 1.5 μM antibodies and 15 μM substrate. Fluorescence intensity was measured immediately after and ten minutes after the mixing at λ ex 340 nm and λ em 415 nm to determine the change of intensity in ten minutes. Based on the magnitude of the change in ten minutes, 14 antibodies having the catalytic activity were selected. The results obtained are shown in the following Table 1.

TABLE 1

| Antibodies | 10-minute change in fluorescence intensity |
|---|---|
| 7G12 | 12.54 |
| 10C8 | 9.40 |
| 6C4 | 8.00 |
| 6B12 | 7.20 |
| 10B2 | 7.10 |
| 7H1 | 6.40 |
| 2E1 | 5.04 |
| 4G9 | 4.08 |
| 8H10 | 3.49 |
| 8A11 | 3.40 |
| 5H2 | 2.88 |
| 3G2 | 2.31 |
| 9F9 | 2.20 |
| 6G10 | 2.08 |

2. Determination of Enantioselectivity of Catalytic Antibodies by Measuring Fluorescence.

To a solution of each of 14 antibodies, which were found to be a catalytic antibody, in 50 mM Tris-buffered solution, pH 8.0 (360 μL), was added a solution of one of the compounds (L-10) and (D-10), which were respectively prepared in Preparations 1 and 2, in 150 μM DMSO solution (40 μL) at 25° C., and they were mixed with stirring to obtain the reaction mixture containing 1.5 μM antibody and 15 μM substrate. Fluorescence intensity was immediately after and ten minutes after the mixing, at λ ex 340 nm and λ em 415 nm to determine the change of the intensity in 10 minutes. Based on the magnitude of the change in ten minutes, 10 antibodies having the catalytic activity selective to the L-form and 4 antibodies having a catalytic activity selective to the D-form were identified. The results obtained are shown in the following Tables 2 and 3.

TABLE 2

| Antibodies selective | 10-min. change in fluorescence intensity | |
| --- | --- | --- |
| to L-form | L-10 | D-10 |
| 7G12 | 23.29 | 0.80 |
| 10C8 | 30.45 | 0.48 |
| 6C4 | 10.4 | 0.77 |
| 6B12 | 9.67 | 0.90 |
| 10B2 | 7.90 | 0.96 |
| 7H1 | 8.00 | 1.03 |
| 2E1 | 7.80 | 1.28 |
| 4G9 | 5.67 | 1.12 |
| 8H10 | 5.05 | 0.72 |
| 6G10 | 3.00 | 0.62 |

TABLE 3

| Antibodies selective | 10-min. change in fluorescence intensity | |
| --- | --- | --- |
| to D-form | L-10 | D-10 |
| 3G2 | 0.38 | 4.32 |
| 5H2 | 0.40 | 5.16 |
| 8A11 | 0.30 | 4.62 |
| 9F9 | 0.48 | 4.44 |

Hybridomas producing antibodies 7G12 and 3G2 were named hybridomas ZAA 7G12 and ZAA 3G2, respectively.

Both hybridomas 7G12 and 3G2 were deposited at Fermentation Research Institute Agency of Industrial Science and Tenchnology, Japan, on Dec. 21, 1994, under the Budapest Treaty on the international recognition of the deposit of microorganisms for the purposes of patent procedure, with accession Nos. FERM BP-4947 and FERM BP-4946, respectively.

DNA-base sequences corresponding to variable regions of 7G12 and 3G2 antibodies, in which antigen-binding sites exist, were determined using DyeDeoxy Terminator cycle Sequencing kits (Applied Biosystems) and the corresponding amino acid sequences were also determined.

For antibody 7G12, DNA-base sequence corresponding to and the amino acid sequence for the variable region of the heavy chain are shown in SEQ ID NOs. 1 and 2, respectively, and those for variable region of the light chain in SEQ ID NOs. 3 and 4, respectively. For antibody 3G2, DNA-base sequence and the amino acid sequence for the variable region of the heavy chain are shown in SEQ ID NOs. 5 and 6, respectively, and those for variable region of the light chain in SEQ ID NOs. 7 and 8, respectively.

EXAMINATION 2

Determination of Specificity to Substrate and Enantioselectivity of Monoclonal Antibodies Having Catalytic Activity 1. Determination of Specificity to Substrate and Enantioselectivity of Monoclonal Antibody 7G12 by HPLC.

To a solution of antibody 7G12 in 50 mM Tris-buffered solution, pH 8.0 (90 μL), was added a solution of a substrate compound, N-(benzyloxycarbonyl)-L-phenylalanine 4-nitrobenzyl ester (L-1) (R=PhCH$_2$), synthesized in Preparation 3, in 2mM DMSO solution (10 μL) at 25° C., and they were mixed with stirring to obtain the reaction mixture containing 10.8 μM antibody and 200 μM substrate. By means of HPLC (YMCAM-303: C-18, 10 mm in diameter× 250 mm in length, an aqueous solution of acetonitrile/0.1% trifluoroacetic acid=35/65 (0–7 minutes), 35/65–90/10 (7–15 minutes), 90/10 (15–17 minutes), 1.0 mL/minute, 278 nm), the amount of 4-nitrobenzyl alcohol (retention time: 5.9 minutes) produced in the reaction mixture was traced in time course for the purpose of determing initial rate. Next, the same procedure as mentioned above was repeated using N-(benzyloxycarbonyl)-D-phenylalanine 4-nitrobenzyl ester (D-1) (R=PhCH$_2$) instead of N-(benzyloxycarbonyl)-L-phenylalanine 4-nitrobenzyl ester (L-1) (R=PhCH$_2$) to determine the initial rate. Background hydrolytic reaction rate was also determined based on the amount of 4-nitrobenzyl alcohol produced by spontaneous degradation in the reaction solution free from antibody 7G12.

In the above-experiment where antibody 7G12 was used, background hydrolytic reaction rate was subtracted from the initial hydrolytic reaction rate for L- and D-forms of the substrate (R=PhCH$_2$) to determine the net initial hydrolytic reaction rate of antibody 7G12. The antibody 7G12 did not catalyze the hydrolysis of D-form of substrate (D-1) (R=PhCH$_2$). Thus, the antibody 7G12 enantioselectively catalyzed the hydrolysis of the substrate.

The specificity to substrate and enantioselectivity of the antibody 7G12 were extensively studied, according to the same procedure as mentioned above, using other substrates derived from alanine, leucine, norleucine, methionine, valine, phenylglycine, 4-hydroxyphenylglycine and lysine, synthesized in Preparation 3, and it was found that the antibody 7G12 enantioselectively catalyzed the hydrolysis of L-form of the substrates. The following Table 4 shows the initial hydrolytic rate as well as background reaction rate constants for L-form of the substrates.

TABLE 4

| Hydrolysis of L-amino acid ester derivatives by antibody 7G12 | | | | |
| --- | --- | --- | --- | --- |
| Substrate | Background reaction rate | Concentration for reaction | | Initial rate |
| L-1 (R—) | constants κuncat (min$^{-1}$) | Antibody 7G12 (μM) | L-1 (μM) | V (μM/min.) |
| CH$_3$— | 1.06 × 10$^{-4}$ | 10 | 200 | 3.49 × 10$^{-1}$ |
| (CH$_3$)$_2$CHCH$_2$— | 1.26 × 10$^{-5}$ | 10 | 200 | 6.20 × 10$^{-1}$ |
| CH$_3$(CH$_2$)$_3$— | 1.71 × 10$^{-5}$ | 5 | 100 | 3.74 × 10$^{-2}$ |
| CH$_3$SCH$_2$CH$_2$— | 3.83 × 10$^{-5}$ | 10 | 200 | 7.73 × 10$^{-1}$ |
| PhCH$_2$— | 2.24 × 10$^{-5}$ | 10 | 200 | 3.85 × 10$^{-1}$ |
| (CH$_3$)$_2$CH— | 6.47 × 10$^{-6}$ | 5 | 100 | 5.54 × 10$^{-3}$ |
| Ph— | 5.62 × 10$^{-3}$ | 5 | 100 | 7.83 × 10$^{-1}$ |
| 4—HOPh— | 1.84 × 10$^{-4}$ | 5 | 200 | 3.33 × 10$^{-1a)}$ |
| H$_2$N(CH$_2$)$_4$— | 1.40 × 10$^{-4}$ | 5 | 100 | 4.36 × 10$^{-1}$ | a)Reacted with DL-1 as a substrate.

2. Determination of Specificity to Substrate and Enantioselectivity of Monoclonal Antibody 3G2 by HPLC.

Specificity to substrate and enantioselectivity of antibody 3G2 were determined according to the same procedure as that used for antibody 7G12, and it was found that said antibody enantioselectively catalyzed the hydrolysis of D-form of substrates derived from alanine, phenylalanine, leucine, norleucine, methionine, valine, phenylglycine, and 4-hydroxyphenylglycine, synthesized in Preparation 3. The following Table 5 shows the initial hydrolytic rate for D-form of the substrates. The background reaction rate constants are the same as those shown in Table 4.

TABLE 5

Hydrolysis of D-amino acid ester derivatives (D-1) by antibody 3G2.

| Substrate | Concentration for reaction | | Initial rate |
|---|---|---|---|
| D-1 (R—) | Antibody 3G2 ($\mu M$) | D-1 ($\mu M$) | V ($\mu M$/min.) |
| $CH_3$— | 5 | 100 | $9.31 \times 10^{-2}$ |
| $(CH_3)_2CHCH_2$— | 10 | 100 | $1.16 \times 10^{-1}$ |
| $CH_3(CH_2)_3$— | 10 | 100 | $9.12 \times 10^{-2}$ |
| $CH_3SCH_2CH_2$— | 10 | 100 | $2.15 \times 10^{-1}$ |
| $PhCH_2$— | 5 | 50 | $1.54 \times 10^{-2}$ |
| $(CH_3)_2CH$— | 10 | 100 | $1.96 \times 10^{-3}$ |
| Ph— | 5 | 100 | $2.91 \times 10^{-2}$ |
| 4—HOPh— | 10 | 100 | $4.08 \times 10^{-1}$ |

What is claimed is:

1. The process for optically resolving a racemic mixture of amino acid derivatives, comprising using a nonspecific catalytic antibody which enantioselectively hydrolyzes various amino acid ester derivatives.

2. The process of claim 1 wherein the amino acid ester derivative is a 4-nitrobenzyl ester.

3. The process of claim 1 or wherein the amino acid ester derivative is amino-protected.

4. The process of claim 1 wherein the amino acid ester derivative has the formula (L-1):

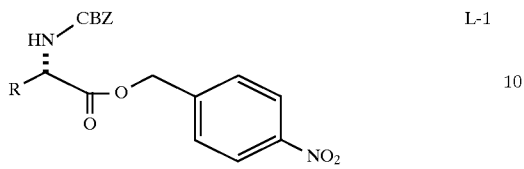

wherein CBZ is N-benzyloxycarbonyl and

R is an alkyl or phenyl group which is optionally substituted with hydroxy, amino, alkylthio, acyloxy, or phenyl.

5. The process of claim 4 R of the formula (L-1) is CH$_3$—, phCH$_2$—, (CH$_3$)$_2$CHCH$_2$—, CH$_3$(CH$_2$)$_3$—, CH$_3$SCH$_2$CH$_2$—, (CH$_3$)$_2$CH—, ph—, or 4—HOph—.

6. The process of claim 1 wherein the amino acid ester derivative has the formula (D-1):

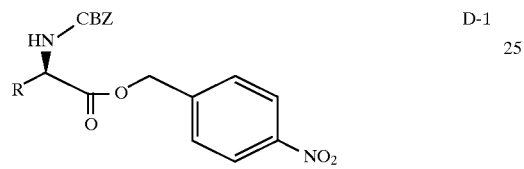

wherein CBZ is N-benzyloxycarbonyl and R is an alkyl or phenyl group which is optionally substituted with hydroxy, amino, alkylthio, acyloxy, or phenyl.

7. The process of claim 6 wherein the R of the formula (D-1) is CH$_3$—, phCH$_2$—, (CH$_3$)CHCH$_2$—, CH$_3$(CH$_2$)$_3$—,CH$_3$SCH$_2$CH$_2$CH—, (CH$_3$)$_2$CH—, ph—, or 4—HOph—.

8. The process of claim 1 or 2 wherein the catalytic antibody is produced by stimulation with an antigen comprising a compound of the formula (3):

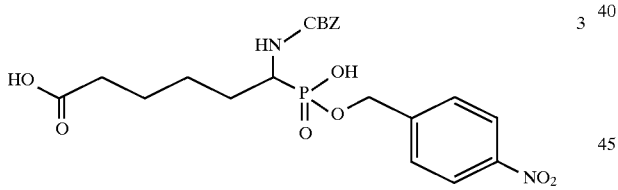

wherein CBZ is N-benzyloxycarbonyl.

9. The process of claim 8 wherein the catalytic antibody is produced by hybridoma ZAA 7G12.

10. The process of claim 8 wherein the catalytic antibody is produced by hybridoma 3G2.

11. The process for preparing an optically active amino acid comprising the steps of:
a) subjecting a racemic mixture of amino acid derivatives to an ester forming reaction to form amino acid ester derivatives;
b) selectively hydrolyzing a desired stereoisomer, D- or L-isomer, of the amino acid ester derivatives with a nonspecific catalytic antibody which enantioselectively hydrolyzes various amino acid ester derivatives; and
c) treating the resulting hydrolyzed mixture to isolate the desired hydrolyzed stereoisomer of the amino acid ester derivatives thereby preparing the optically active amino acid.

12. The process of claim 11 wherein the resulting hydrolyzed mixture is treated by being made acidic or basic, followed by extracting with an organic solvent to obtain an aqueous layer from which the desired hydrolyzed stereoisomer is isolated.

13. The process of claim 11 wherein the amino acid ester derivative is 4-nitrobenzyl ester.

14. The process of claim 11 wherein the amino acid ester derivative is amino-protected.

15. The process of claim 11 wherein the amino acid ester derivative is a compound having the formula (L-1):

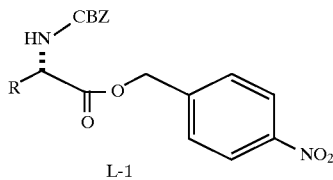

wherein CBZ is N-benzyloxycarbonyl and

R is an alkyl or phenyl group which is optionally substituted with hydroxy, amino, alkylthio, acyloxy, or phenyl.

16. The process of claim 15 wherein the amino acid ester derivative has the formula (L-1):

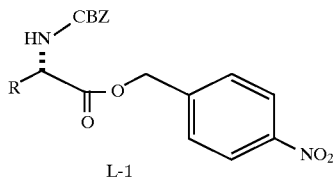

wherein CBZ is N-benzyloxycarbonyl and

R is CH$_3$—, phCH$_2$—, (CH$_3$)$_2$CHCH$_2$—, CH$_3$(CH$_2$)$_3$—, CH$_3$SCH$_2$CH$_2$—, (CH$_3$)$_2$CH—, ph—, or 4—HOph—.

17. The process of claim 11 wherein the amino acid ester derivative has the formula (D-1):

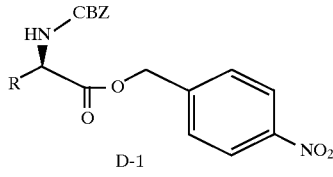

wherein CBZ is N-benzyloxycarbonyl and R is an alkyl or phenyl group which is optionally substituted with hydroxy, amino, alkylthio, acyloxy, or phenyl.

18. The process of claim 17 wherein the amino acid ester derivative has the formula (D-1):

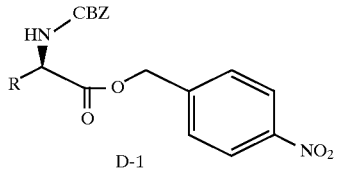

wherein CBZ is N—benzyloxycarbonyl and R is CH$_3$—, phCH$_2$—, (CH$_3$)$_2$CHCH$_2$, CH$_3$(CH$_2$)$_3$—, CH$_3$SCH$_2$CH$_2$—, (CH$_3$)$_2$CH—, ph—, or 4-HOph-.

19. The process of claims 11 or 13 wherein the catalytic antibody is produced by stimulation with an antigen comprising a compound of the formula:

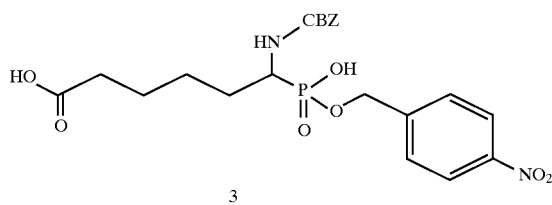

wherein CBZ is N-benzyloxycarbonyl.

20. The process of claim 19 wherein the catalytic antibody is produced by hybridoma ZAA 7G12.

21. The process of claim 19 wherein the catalytic antibody is produced by hybridoma ZAA 3G2.

22. A catalytic antibody produced by stimulation with an antigen comprising a compound of the formula:

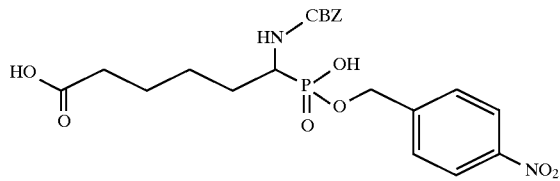

wherein CBZ is N-benzyloxycarbonyl.

23. The catalytic antibody of claim 22 produced by hybridoma ZAA 7G12.

24. The catalytic antibody of claim 22 produced by hybridoma ZAA 3G2.

25. A hybridoma producing the catalytic antibody of claim 22.

26. The hybridoma of claim 25 designated ZAA 7G12.

27. The hybridoma of claim 25 designated ZAA 3G2.

28. A catalytic antibody produced by stimulation with an antigen comprising a compound of the formula:

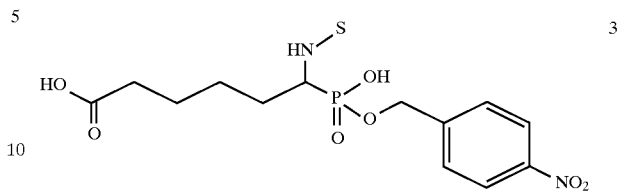

wherein S is an amino protecting group.

29. The catalytic antibody of claim 28 wherein S is trichloroacetyl, benzyl, t-butoxycarbonyl, or 9-fluorenylmethoxycarbonyl.

30. A catalytic antibody produced by stimulation with an antigen comprising a compound of the formula:

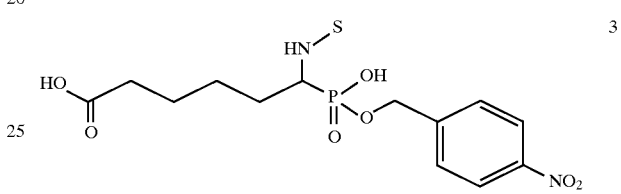

wherein S is a phenyl moiety which is substituted with lower alkyl, lower alkoxy, halogen or nitro.

* * * * *